US006766187B1

(12) United States Patent
Black et al.

(10) Patent No.: US 6,766,187 B1
(45) Date of Patent: Jul. 20, 2004

(54) METHOD FOR DETECTING COAGULATION IN LASER TREATMENT OF BLOOD VESSELS

(75) Inventors: John F. Black, San Mateo, CA (US); Jennifer K. Barton, Tucson, AZ (US)

(73) Assignee: Lumenis Inc., New York, NY (US)

( * ) Notice: Subject to any disclaimer, the term of this patent is extended or adjusted under 35 U.S.C. 154(b) by 67 days.

(21) Appl. No.: 09/664,193

(22) Filed: Sep. 18, 2000

(51) Int. Cl.[7] .............................................. A61B 6/00
(52) U.S. Cl. ........................ 600/473; 600/476; 600/504
(58) Field of Search ................................ 600/476, 473, 600/474, 475, 477, 479, 480, 500, 504, 505, 506

(56) References Cited

U.S. PATENT DOCUMENTS

| | | | | |
|---|---|---|---|---|
| 4,773,097 A | * | 9/1988 | Suzuki et al. | ............... 600/476 |
| 6,165,170 A | * | 12/2000 | Wynne et al. | ................. 606/9 |
| 6,289,236 B1 | * | 9/2001 | Koenig et al. | .............. 600/473 |
| 6,505,059 B1 | * | 1/2003 | Kollias et al. | .............. 600/316 |
| 6,522,911 B1 | * | 2/2003 | Toida et al. | ................ 600/473 |

FOREIGN PATENT DOCUMENTS

| | | | | |
|---|---|---|---|---|
| JP | 56-137140 | * | 10/1981 | ................ 356/446 |
| JP | 60-006871 | * | 1/1985 | |

OTHER PUBLICATIONS

O. Pomerantzeff et al., "A Method to Predetermine the Correct Photocoagulation Dosage," *Arch Ophthalmol*, vol. 101, Jun. 1983, pp. 949–953.

J.H.C. Inderfurth et al., "Dynamic Reflectometer for Control of Laser Photocoagulation on the Retina," *Lasers in Surgery and Medicine*, vol. 15, No. 1, 1994, pp. 54–61.

Y. Yang et al., "Automatic Control of Lesion Size in a Simulated Model of the Eye," *IEEE Journal of Quantum Electronics*, vol. 26, No. 12, Dec. 1990, pp. 2232–2239.

M.R. Jerath et al., "Reflectance Feedback Control of Photocoagulation In Vivo," *Arch Ophthalmol*, vol. 111, Apr. 1993, pp. 531–534.

W.J. Geeraets et al., "Light Reflectance of the Ocular Fundus," *Archives of Ophthalmology*, vol. 69, May 1963, pp. 612–617.

W.S. Weinberg et al., "The Change in Light Reflection of the Retina During Therapeutic Laser–Photocoagulation," *IEEE Journal of Quantum Electronics*, vol. QE–20, No. 12, Dec. 1984, pp. 1481–1489.

R. Birngruber et al., "Fundus Reflectometry: A Step towards Optimization of the Retina Photocoagulation," *Mod. Probl. Ophthal.*, vol. 18, 1977, pp. 383–390.

M.R. Jerath et al., "Calibrated real–time control for lesion size based on reflectance images," *Applied Optics*, vol. 32, No. 7, Mar. 1, 1993, pp. 1200–1209.

(List continued on next page.)

*Primary Examiner*—Philip H. Leung
(74) *Attorney, Agent, or Firm*—Eitan, Pearl, Latzer & Cohen Zedek, LLP (57) ABSTRACT

Onset of coagulation of blood in a blood vessel irradiated by electromagnetic radiation is detected by directing light at the blood vessel and monitoring the intensity of a portion of the light remitted from the blood vessel. An increase or decrease in the monitored light intensity indicates the onset of coagulation. The increase or decrease results from the formation of methemoglobin in the blood which accompanies the onset of coagulation. The methemoglobin is formed by photo conversion or thermal conversion of normal blood oxyhemoglobin. The wavelength of the monitoring light is selected to be different from that of the electromagnetic radiation and is preferably a wavelength for which the ratio of its absorptivity in hemoglobin and its absorptivity in normal blood is less than about one-half or greater than about two.

24 Claims, 4 Drawing Sheets

OTHER PUBLICATIONS

O. Pomerantzeff et al., "Time and Location Analysis of Lesion Formation in Photocoagulation," *Arch Ophthalmol,* vol. 101, Jun. 1983, pp. 954–957.

D.J. Smithies et al., "The Effect of the Illumination Time When Treating Port–wine Stains," *Lasers in Medical Science,* vol. 10, No. 2, Jun. 1995, pp. 93–104.

S. Gabay et al., "Modelling the Assessment of Port Wine Stain Parameters From Skin Surface Temperature Following a Diagnostic Laser Pulse," *Lasers in Surgery and Medicine,* vol. 20, No. 2, 1997, pp. 179–187.

C.H.G. Wright et al., "Initial in vivo results of hybrid retinal photocoagulation system," *Journal of Biomedical Optics,* vol. 5, No. 1, Jan. 2000, pp. 56–61.

S. Mordon et al., "Relation Between Skin Surface Temperature and Minimal Blanching During Argon, Nd–YAG 532, and CW Dye 585 Laser Therapy of Port–Wine Stains," *Lasers in Surgery and Medicine,* vol. 13, No. 1, 1993, pp. 124–126.

G.D. Lewis et al., "Backscattering target detection in a turbid medium by polarization discrimination," *Applied Optics,* vol. 38, No. 18, Jun. 20, 1999, pp. 3937–3944.

T.E. Milner et al., "Depth determination of chromophores in human skin by pulsed photothermal radiometry," *Applied Optics,* vol. 35, No. 19, Jul. 1, 1996, pp. 3379–3385.

R.R. Anderson et al., "Pulsed photothermal radiometry in turbid media: internal reflection of backscattered radiation strongly influences optical dosimetry," *Applied Optics,* vol. 28, No. 12, Jun. 15, 1989, pp. 2256–2262.

A. Kienle et al., "Why do veins appear blue? A new look at an old question," *Applied Optics,* vol. 35, No. 7, Mar. 1, 1996, pp. 1151–1160.

T.E. Milner et al., "Depth profiling of laser–heated chromophores in biological tissues by pulsed photothermal radiometry," *Journal of the Optical Society of America A,* vol. 12, No. 7, Jul. 1995, pp. 1479–1488.

Y. Yang et al., "Reflectance as an Indirect Measurement of the Extent of Laser–Induced Coagulation," *IEEE Transactions on Biomedical Engineering,* vol. 37, No. 5, 1990, pp. 466–473.

\* cited by examiner

METHOD FOR DETECTING COAGULATION IN LASER TREATMENT OF BLOOD VESSELS

TECHNICAL FIELD OF THE INVENTION

The present invention relates in general to laser treatment of biological tissues and structures including blood vessels. The invention relates in particular to methods of detecting onset of coagulation in the blood vessels.

DISCUSSION OF BACKGROUND ART

In recent years, use of lasers for treatment of dermatological conditions and other conditions involving blood vessels has rapidly gained acceptance by the medical community. By way of example, lasers delivering light in the green and yellow regions of the visible spectrum are now effectively used to treat vascular disorders. The green and yellow wavelengths between about 530 and 590 nanometers (nm) are particularly favored because absorption of these wavelengths in blood hemoglobin is significantly higher than in the skin pigment melanin. This allows the hemoglobin to be selectively targeted by the radiation in a treatment often referred to as selective photothermolysis. In such a treatment, blood in targeted vessels is coagulated by heat generated when the green or yellow light is absorbed in the blood hemoglobin. This results in necrosis of the vessels in the treated area. The coagulated or necrotized vessels are eventually reabsorbed by the body and replaced with scar tissue.

One problem encountered in applying laser treatment is determining a light dosage sufficient to effect the required coagulation. This can vary from patient to patient depending on factors such as melanin content of the skin (skin color), the size (diameter) of blood vessels being treated and the depth of the blood vessels in the skin. Extending dosage beyond that required to effect coagulation can lead to complications including scarring, scabbing, edema and epidermal damage or extravasation of red blood cells from a vessel being treated. Extravasation can lead to formation of progressive purpura which will eventually disappear, but which are generally cosmetically unacceptable to patients under most circumstances.

An increase in reflection and scatter of treatment radiation has been observed in connection with lesion formation in retinal photocoagulation. Skin, however, is highly scattering of yellow/green radiation. Accordingly any increase in reflection or scatter resulting from coagulation of blood in a blood vessel in or under the skin will be difficult to discriminate from background scatter and reflection. Accordingly there is need for a method of detecting the onset of coagulation which effectively discriminates against background scatter and reflection of treatment radiation.

SUMMARY OF THE INVENTION

The present invention is directed to a method of detecting onset of coagulation of blood in a blood vessel irradiated by electromagnetic radiation having a selected treatment wavelength. The method comprises directing electromagnetic radiation having a selected monitoring wavelength to the blood vessel, the monitoring wavelength being different from the treatment wavelength. A portion of the monitoring radiation remitted from the blood vessel is detected. One of an increase and decrease in the detected remitted monitoring radiation is interpreted as an indication of the onset of coagulation of blood in the blood vessel.

The method of the present invention is based on detecting a change in absorptivity of blood irradiated by the treatment wavelength characteristic of conversion of oxyhemoglobin and de-oxyhemoglobin in the normal blood to methemoglobin. Depending on the wavelength the absorptivity of methemoglobin can be higher or lower than the absorptivity of normal blood. By way of example, in a wavelength range between about 525 and 580, methemoglobin has a lower absorptivity than normal blood. In wavelength ranges between about 610 and 660 nm and between about 800 and 1000 nm, methemoglobin has a higher absorptivity than normal blood.

In one preferred embodiment of the inventive method, the monitoring wavelength is selected such that the absorptivity thereof in normal blood is greater than or equal to about two times the absorptivity thereof in methemoglobin, and an increase in the detected remitted monitoring radiation is interpreted as an indication of the onset of coagulation of blood in the blood vessel. In another preferred embodiment of the inventive method, the monitoring wavelength is selected such that the absorptivity thereof in normal blood is less than or equal to about one-half the absorptivity thereof in methemoglobin, and a decrease in the detected remitted monitoring radiation is interpreted as an indication of the onset of coagulation of blood in the blood vessel.

One application of the method of the present invention is in dermal treatments wherein the wavelength of treatment radiation is in a range between about 510 and 585 nm, for example, the 532 nm radiation of a frequency-doubled Nd:YAG laser. Here, a preferred monitoring wavelength is selected in a range between about 610 and 660 nm.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

DETAILED DESCRIPTION OF THE INVENTION

As noted above, a principle of the present invention involves optically detecting formation of methemoglobin in blood in a blood vessel being irradiated with electromagnetic radiation. In one exemplary treatment of a vascular disorder, the vessel is irradiated to heat the blood to a temperature that causes coagulation of the blood. A goal of the treatment is to cause sufficient coagulation that flow of blood through the blood vessel is prevented by the coagulated blood or coagulum.

It has been determined that heating of the blood to the temperature at which coagulum forms causes a change of at least a portion of hemoglobin in the blood vessel from a normal (oxyhemoglobin) form to methemoglobin. The change may be made via an intermediate change of oxyhemoglobin to de-oxyhemoglobin. In its "normal" state, blood includes oxyhemoglobin and de-oxyhemoglobin, with oxyhemoglobin in a proportion of about 70% or greater. Venous blood includes oxyhemoglobin and de-oxyhemoglobin respectively in about a 70:30 ratio. Arterial blood usually includes close to 100% oxyhemoglobin.

Figure 1:
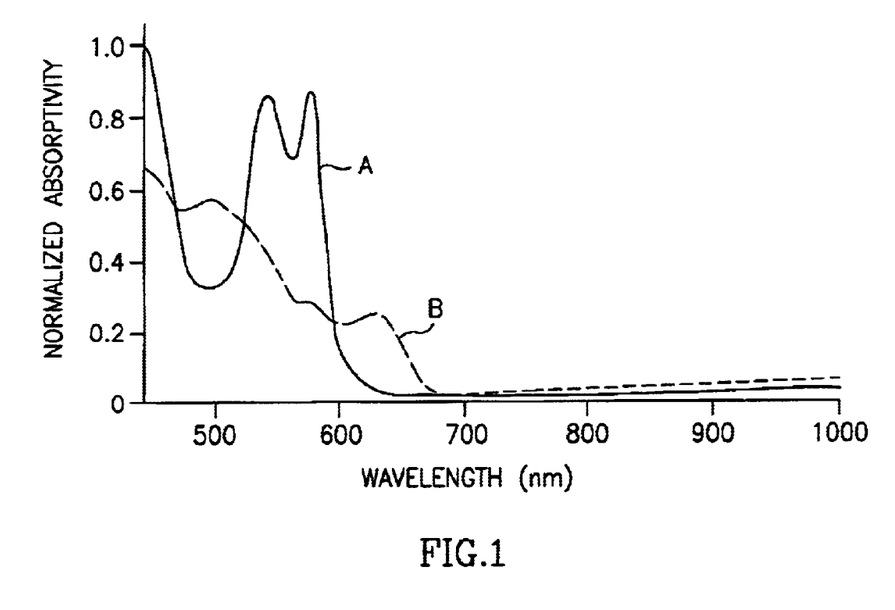
FIG. 1 is graph schematically illustrating absorptivity of normal blood and methemoglobin in a wavelength range between about 450 and 1000 nm.

Turning now to the drawings, in FIG. 1, normalized absorption spectra of normal blood (curve A) and methemoglobin (curve B) for visible light in a wavelength range between about 450 nm and 1000 nm are schematically graphically depicted. It can be seen that the absorption spectra of normal blood and methemoglobin are substantially different. Outside of the wavelength region containing the preferred treatment beam (532 nm), the red region of the visible spectrum (between about 610 nm and 660 nm and particularly at a wavelength of about 635 nm) demonstrates a significant relative difference in absorption. The relative difference in absorptivity is comparable at wavelengths of 800 nm and longer, however the absolute absorption coefficients at these wavelengths are about an order of magnitude smaller. In the regions between 610 and 660 nm and 800 to at least 1000 nm, methemoglobin has a higher absorptivity than normal blood. Although not indicated in FIG. 1, methemoglobin has a higher absorption than normal blood at wavelengths up to at least 1350 nm. As noted above, radiation having a wavelength in the yellow-green spectral region between about 485 nm and 590 nm, in particular in the range between about 525 nm and 580 nm where absorption of oxyhemoglobin and de-oxyhemoglobin (normal blood) is highest is a preferred wavelength for laser treatment of vascular disorders. In the 525 nm and 580 nm region there is also a significant difference in absorptivity between methemoglobin and normal blood, with normal blood in this region having the higher absorptivity.

Figure 2:
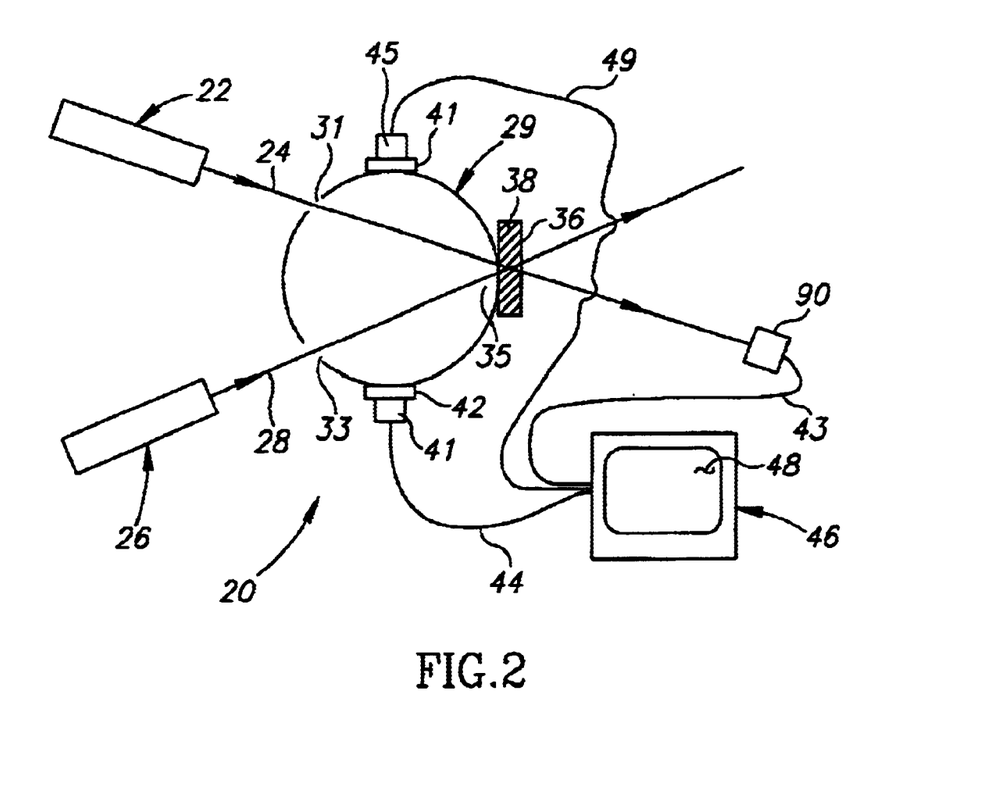
FIG. 2 schematically illustrates an experimental arrangement for measuring change in transmission and remittance of 633 nm CW laser radiation through blood as a result of the onset of coagulation caused by pulsed irradiation of the blood with 532 nm radiation.

Referring now to FIG. 2, in order to test principles of the present invention, an experimental apparatus 20 was arranged to observe a change in absorption of blood for red light corresponding to irradiation of the blood with yellow-green radiation. Apparatus 20 includes a helium-neon (He—Ne) laser 22 delivering a beam 24 of continuous wave (CW) electromagnetic radiation (light) at a wavelength at about 633 nm. Apparatus 20 also includes a frequency-doubled neodymium-doped YAG (Nd:YAG) laser 26 arranged to deliver a beam 28 pulsed electromagnetic radiation at a wavelength of about 532 nm.

Beams 24 and 28 are projected through an integrating sphere 29 via apertures 31, 33 and 35 therein and arranged to overlap in a cuvette 36 including a sample of whole blood 38, diluted in a ratio 1:1 with isotonic saline. The thickness D of whole blood sample 38 is about 200.0 micrometers ($\mu$m). A detector 40 is arranged to monitor the intensity of 633 nm light transmitted through cuvette 36.

Remitted 532 nm light and remitted 633 nm light from blood sample 32 are collected by integrating sphere 29. In this description and the appended claims, the terminology "remitted light" refers collectively to light which has been reflected, diffusely reflected, backscattered or otherwise re-emitted. The collected remitted 532 nm light and 633 nm light are sampled by detectors 41 and 45 respectively. A filter arrangement 42 (a combination of neutral-density filters and a spectrally selective filter) excludes remitted 633 nm light from detector 41. A similar filter arrangement 47 excludes remitted 532 nm light from detector 45. Output of detectors 40, 41 and 45 is communicated by leads 43, 44 and 49 respectively to a monitor 46. Monitor 46 includes a display 48 on which the outputs of detectors 40, 41, and 45 can be simultaneously displayed.

Figure 3:
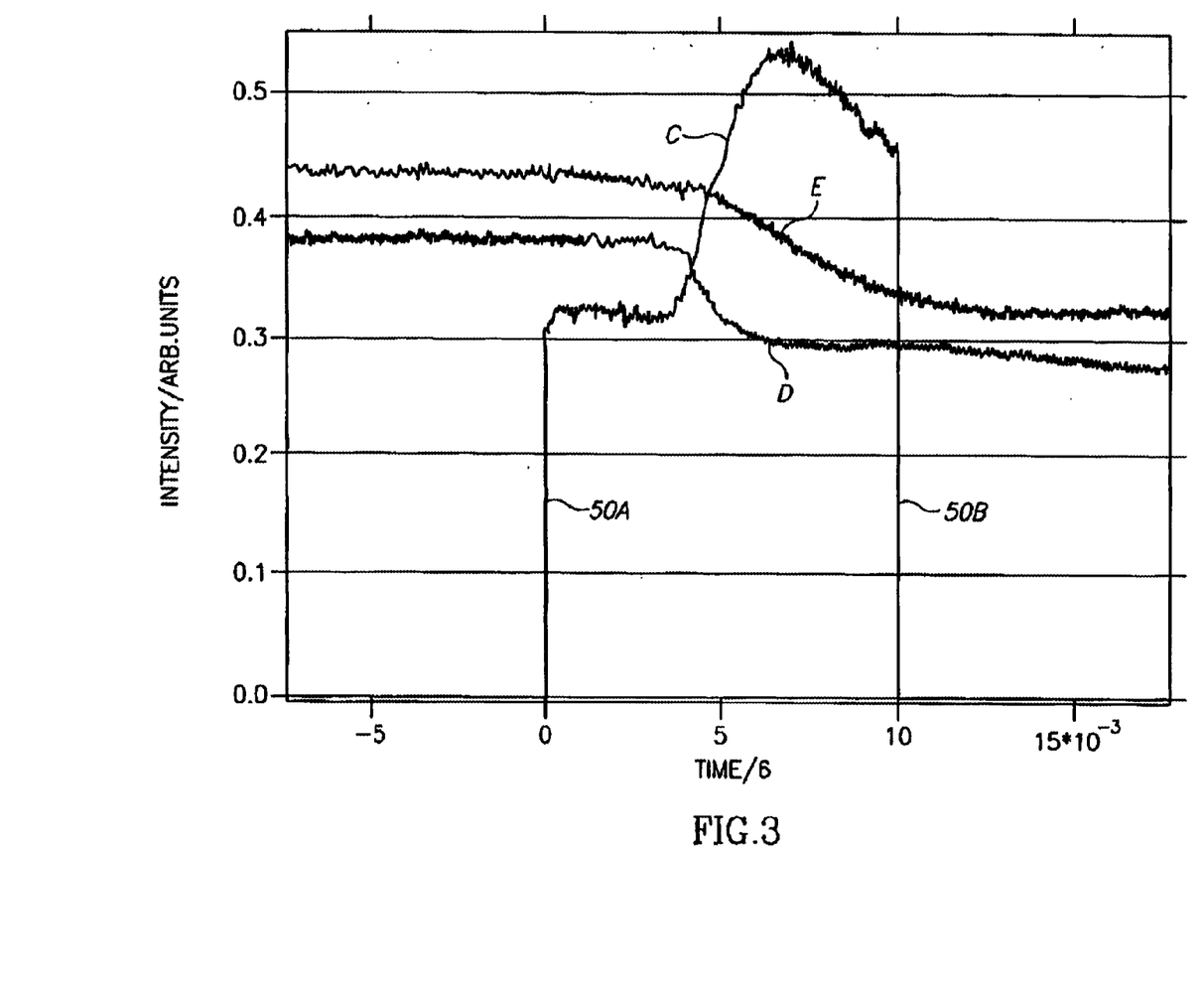
FIG. 3 is a graph schematically illustrating remittance and transmission of 633 nm radiation and remitted 532 nm radiation in the experimental arrangement of FIG. 2.

One experimental result produced by apparatus 20 is schematically, graphically illustrated in FIG. 3. Here curve C depicts the output of detector 41 during delivery of a pulse of 532 nm light having a duration of about 10.0 milliseconds (ms). The initiation and termination of the pulse are indicated by lines 50A and 50B respectively. Curves D and E depict the output of detectors 40 and 45 respectively, prior to, during and following delivery of the 532 nm light-pulse.

It can be seen that about four milliseconds after initiation 50A of the pulse (due in part at least to an increase in temperature of blood 38 resulting from absorption thereby of the 532 nm radiation) the intensity of the remitted 532 nm light begins to increase. This is indicative of the onset of coagulation. Consistent with this, the intensity of transmitted 633 nm light begins a sharp decrease which can be inferred to be due to an attendant conversion of oxyhemoglobin and/or de-oxyhemoglobin to methemoglobin. Correspondingly there is a decrease in the intensity of remitted 633 nm light.

Clearly, both the change in intensity of 532 nm radiation and the change in intensity of 633 nm radiation in the above-described experiment are indicative of an onset of coagulation. In practice, it is expected that an observed relative change in 532 nm light intensity would be significantly less than is indicated by curve C due to scattering of the radiation from tissue surrounding a blood vessel (blood vessels) being irradiated. This could lead to uncertainty of detection. The 633 nm light, however, can be focussed on a blood vessel in a treatment area and the corresponding remitted 633 nm light measured with a confocal detection arrangement to minimize the possibility of an error in detection. One such confocal detection arrangement is described hereinbelow.

The selection of CW radiation for monitoring the onset and progress of coagulation and the fact that coagulation dynamics can be observed even after a treatment pulse is terminated are particularly advantageous in the method of the present invention. One general advantage, of course, is that there is no requirement to synchronize delivery of treatment and monitoring light. One particular advantage is in being able to monitor progress of coagulation when treatment radiation is delivered as a sequence, train or burst of pulses as is not uncommon in the art.

Such a train of pulses is typically delivered in a manner such that the heating effect is cumulative such that the progress of coagulation can continue between pulses. The ability to monitor the progress of coagulation between pulses combined with a suitable feedback arrangement between the coagulation monitoring and a light source delivering of the pulses allows a pulse sequence to be terminated if it is determined after delivery of one pulse that a subsequent pulse is not necessary to complete coagulation.

It should be noted here that the selection of CW radiation for monitoring purposes in this experiment should not be considered as limiting the present invention. Alternatively, for example, the monitoring radiation may be pulsed radiation or chopped CW radiation at a pulse-frequency or chopping-frequency which facilitates detection with a lock-in amplifier or the like.

Figure 4:
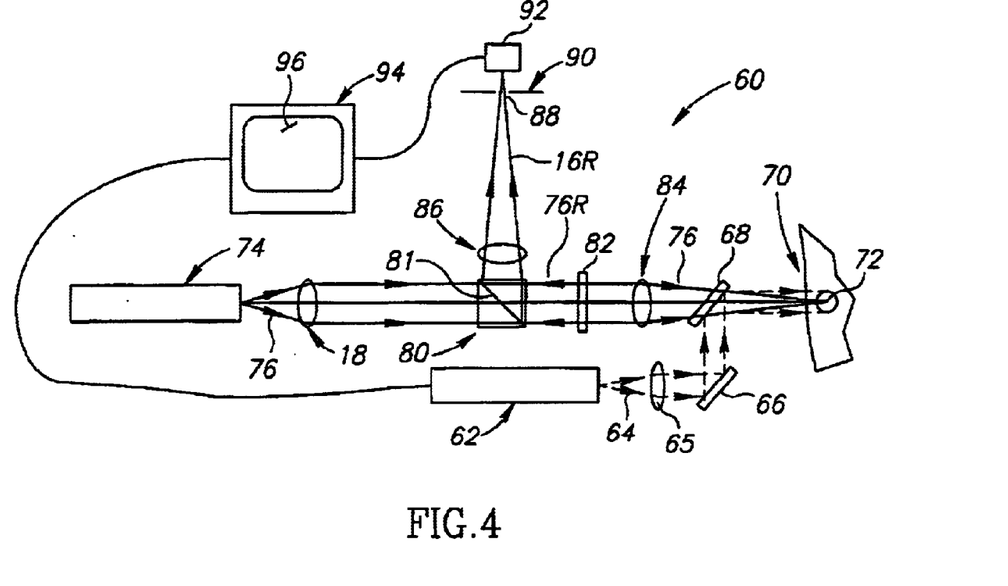
FIG. 4 schematically illustrates one preferred embodiment of apparatus in accordance with the present invention for detecting onset of coagulation in laser dermal treatment.

FIG. 4 schematically depicts one preferred embodiment 60 of apparatus for detecting the onset of coagulation in accordance with the method of the present invention, including a feedback arrangement as discussed above. Apparatus 60 includes a first light-source 62 delivering treatment light (indicated by dotted lines 64) at a wavelength in the region between about 485 and 590 nm. Light-source 62, for example, may be an argon (gas) laser delivering light at a wavelength of about 515 nm, a solid state laser delivering light at a wavelength of about 532 nm as described above, or a dye laser delivering light at a wavelength of about 580 nm. Light 64 from light source 62 is directed via a lens 65, a turning mirror 66 and a dichroic mirror 68 to a region of tissue 70 including a blood vessel 72 to be treated.

It is not intended that the present invention be limited by the light source providing the treatment (coagulating) radiation. Light source 62 may also be a source of non-coherent light such as a gas discharge lamp, with appropriate spectral filtering, if necessary. Indeed, the exemplified treatment wavelength range itself should not be considered as limiting the method of the present invention.

Continuing with reference to FIG. 4, apparatus 60 includes a second light source 74 delivering monitoring light 76 at a wavelength between about 610 and 660 nm or alternatively between about 800 and 1000 nm. One preferred light source is a He—Ne laser delivering light at a wavelength of about 633 nm. Other useful light sources include a krypton (Kr) laser emitting at a wavelength of about 647 nm, and a frequency doubled Nd:YAG laser emitting at a wavelength of about 660 nm. Diode-lasers emitting at 660 nm, 630 nm or a wavelength in the range 800 to 1000 nm are also useful. Diode-lasers emitting (exclusively) at 808 nm, 941 nm, and 975 nm are readily commercially available. Beam shaping optics 78 collimate light 76 and direct the light through a polarizing beamsplitter 80, and a quarter-wave plate (polarization rotator) 82 to focussing optics 84. Focussing optics 84 focus monitoring light 76 through dichroic mirror 68 onto blood vessel 72.

Monitoring light 76R remitted from blood vessel 72 is collimated by focussing optics and directed back through quarter-wave plate 82 to polarizing beamsplitter 80. The polarization of the remitted light having been rotated 90° by the double passage through quarter-wave plate 82, is reflected by polarizing surface 81 of the polarizing beamsplitter and is incident on focussing optics 86. Focussing optics 86 focus light 76R into a "pinhole" aperture 88 of a spatial filter 90. A detector 92 is located behind spatial filter 90 in the direction of propagation of remitted light 76R for receiving the monitored light. Some optimization of light returned from the vessel may be accomplished experimentally by adjusting the orientation of quarter-wave plate 82.

Spatial filter 90 serves to minimize the amount of light reaching detector 92 that has been scattered from tissue surrounding blood vessel 72 by making apparatus 60 truly "confocal". Scattered light from sites adjacent the blood vessel are rejected by the spatial selectivity of the spatial filter. The scattered light, if not filtered out, would reduce the relative reduction in monitoring light observed as a result of formation of methemoglobin in blood vessel 72. The optical filtering effect of dichroic mirror 68, together with spatial filter 90, minimizes the possibility of scattered treatment light reaching detector 92. Output of detector 92 is communicated to a controller 94 including a display 96. Controller 94 electronically communicates with light source 62 such that the output of detector 92 can be used to control the light-source.

Locating the focus of monitoring light 76 on blood vessel 72 may be accomplished by activating light source 74 and scanning the focussed beam of monitoring light over the tissue region to be treated, while simultaneously observing the output of detector 92 on display 96. A small but perceptible drop in output will be observed as the focus of beam 76 intercepts the blood vessel.

The inventive method of detecting the onset of coagulation has several useful applications in dermatological treatment by irradiation with electromagnetic radiation. These applications are not only useful in above discussed treatments where coagulation of blood in blood vessels is a functional part of the treatment, but are useful in other treatments such as non-ablative reduction of wrinkles wherein blood and surrounding tissue are heated by the irradiation but coagulation is to be avoided.

By way of example, test irradiations of an area to be treated can be made beginning with a relatively low dosage and gradually increasing the dosage until the onset of coagulation is detected. This can be defined as determining a coagulation threshold. If a desired result of the treatment is coagulation, then this determination of a coagulation threshold can provide an indication of a dose suitable for achieving coagulation, but with a minimum probability of causing side effects such as scarring or extravasation. If a desired result is to avoid coagulation this threshold can be used to determine a dosage which will achieve this result.

Using the feedback arrangement of apparatus 60, for example, controller 94 may be arranged to shut off treatment light source 62 immediately after a drop in intensity of monitoring light is detected. Any minimal amount of coagulation occurring before shutting off of the light source or thereafter due to above discussed residual temperature effects would be swept away by blood flow in the blood vessel thereby avoiding a permanent change in condition of the blood vessel.

In an application where coagulation is a desired result, the detection of the onset of coagulation could also be used with the feedback arrangement to control additional dosage required to complete coagulation. This could be achieved for example in a single treatment pulse by determining the time at which the pulse is terminated. Alternatively, it could be used to determine the number and duration of one or more subsequent pulses, of the same or a different wavelength, required to complete coagulation and to initiate and control the subsequent pulses.

Those skilled in the art may find applications of the inventive coagulation detection method, other than above-discussed dermatological applications, without departing from the spirit and scope of the present invention. By way of example, the inventive method may be found useful in monitoring laser (electromagnetic radiation) treatment of tumors and adenomas; aneurysms; occult AMD (age-related macular degeneration) and sub-RPE (retinal pigmented epithelium) pockets; classic AMD breakthrough vessels; internal bleeding or hemorrhaging; and embolisms and thrombi. These treatments need not be restricted to treatment using radiation in the yellow green spectrum, as exemplified above, but may also include treatment using near infrared wavelengths. By way of example, stomach ulcers and cobblestone hemangiomas may be advantageously treated by radiation from a Nd:YAG laser emitting at 1064 nm or 808 nm radiation emitted from a diode-laser or array thereof.

Those skilled in the art will also recognize that, while apparatus 60 is described with reference to using a monitoring wavelength at which methemoglobin has a higher absorptivity than normal blood and detecting a decrease in remitted monitoring light as an indication of the onset of coagulation, the apparatus is equally applicable to using a monitoring wavelength at which methemoglobin has a lower absorptivity than normal blood and detecting an increase in remitted monitoring light as an indication of the onset of coagulation. Preferably the monitoring wavelength selected such that the absorptivity thereof in normal blood is either about one-half or less than the absorptivity thereof in methemoglobin, or at least about twice the absorptivity thereof in methemoglobin.

In applications such as treatment of internal bleeding or hemorrhaging; and embolisms and thrombi, delivery of treatment light to a treatment site is usually effected via an endoscope or the like with treatment radiation being delivered via an optical fiber. The coagulation monitoring method of the present invention may be used in such a treatment by also delivering monitoring light to the treatment site via an optical fiber and the endoscope. One such endoscope arrangement is described below with reference to FIG. 5.

Figure 5:
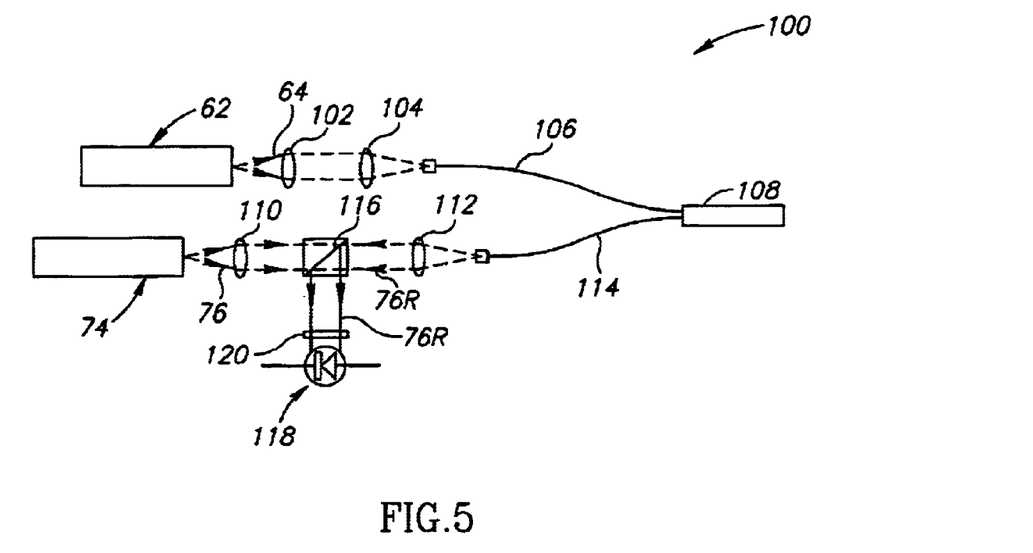
FIG. 5 schematically illustrates another preferred embodiment of apparatus in accordance with the present invention for detecting onset of coagulation in laser treatment via an endoscope.

Here, apparatus 100 in accordance with the present invention includes a laser 62 delivers treatment light 64. Lenses 102 and 104 focus the treatment light into an optical fiber 106 which transports the treatment radiation to an endoscope 108. A laser 74 delivers monitoring light 76. Lenses 110 and 112 focus the monitoring light into an optical fiber 114 which transports the treatment radiation to an endoscope 108. Endoscope 108 is used to deliver the treatment light and monitoring light to a treatment site (not shown). Monitoring light 76R remitted from the treatment site is transported back along optical fiber 114 then collimated by lens 112 and directed by a beamsplitter 116 to a photodiode 118. A filter 120 prevents any backscattered treatment light transported by optical fiber 114 from reaching the photodiode. Signals from the photodiode may be processed and used above for detecting coagulation at the treatment site and controlling delivery of treatment light from laser 62 as described above with respect to apparatus 60 of FIG. 4.

The present invention is described above with reference to a preferred and other embodiments. The invention however is not limited to the embodiments described and depicted. Rather, the invention is limited only by the claims appended hereto.

What is claimed is:

1. A method of detecting onset of coagulation of blood in a blood vessel induced by irradiation of electromagnetic radiation, said electromagnetic radiation having a first wavelength, the method comprising the steps of:
   (a) directing electromagnetic radiation having a second wavelength at the blood vessel, said second wavelength being different from said first wavelength;
   (b) monitoring a portion of said second wavelength radiation remitted from the blood vessel; and
   (c) interpreting one of an increase and decrease in said monitored remitted second wavelength radiation as an indication of the onset of coagulation of blood in the blood vessel.

2. The method of claim 1, wherein said second wavelength is selected such that the absorptivity thereof in normal blood is greater than or equal to about two times the absorptivity thereof in methemoglobin, and wherein an increase in said monitored remitted second-wavelength radiation is interpreted as an indication of the onset of coagulation of blood in the blood vessel.

3. The method of claim 2, wherein said second wavelength is between about 525 and 585 nm.

4. The method of claim 1, wherein said second wavelength is selected such that the absorptivity thereof in normal blood is less than or equal to about one-half the absorptivity thereof in methemoglobin, and wherein a decrease in said monitored remitted second-wavelength radiation is interpreted as an indication of the onset of coagulation of blood in the blood vessel.

5. The method of claim 4, wherein said second wavelength is between about 610 and 660 nm.

6. The method of claim 4, wherein said second wavelength is between about 800 and 1000 nm.

7. A method of detecting onset of coagulation of blood in a blood vessel induced by irradiation of electromagnetic radiation, said electromagnetic radiation having a first wavelength, the method comprising the steps of:
   (a) directing electromagnetic radiation having a second wavelength between about 610 nm and 660 nm at the blood vessel, said second wavelength being different from said first wavelength;
   (b) monitoring a portion of said second wavelength radiation remitted from the blood vessel; and
   (c) interpreting a decrease in said monitored remitted second wavelength radiation as an indication of the onset of coagulation of blood in the blood vessel.

8. The method of claim 7, wherein said second wavelength is about 633 nm.

9. The method of claim 7, wherein said second wavelength is about 647 nm.

10. The method of claim 7, wherein said first wavelength is between about 485 and 590 nm.

11. The method of claim 7, wherein said second-wavelength radiation is CW radiation.

12. The method of claim 7, wherein said second-wavelength radiation is pulsed radiation.

13. A method of detecting onset of coagulation of blood in a blood vessel induced by irradiation of electromagnetic radiation, said electromagnetic radiation having a wavelength between about 485 and 590 nm, the method comprising the steps of:
   (a) directing monitoring electromagnetic radiation having a wavelength between about 610 nm and 660 nm at the blood vessel;
   (b) detecting a portion of said monitoring radiation remitted from the blood vessel; and
   (c) interpreting a decrease in said detected remitted second-wavelength radiation as an indication of the onset of coagulation of blood in the blood vessel.

14. The method of claim 13, wherein said monitoring radiation is CW radiation.

15. A method of detecting onset of coagulation of blood in a blood vessel irradiated by electromagnetic radiation, said electromagnetic radiation having a first wavelength, the method comprising the steps of:
   (a) providing a source of electromagnetic radiation having a second wavelength between about 610 nm and 660 nm, said second wavelength being different from said first wavelength;
   (b) providing a spatial filter having a transmitting aperture therein;
   (c) focussing said second wavelength radiation on the blood vessel;
   (d) focussing a portion of said second wavelength radiation remitted from said blood vessel into said transmitting aperture of said spatial filter;

(e) locating a detector relative to said transmitting aperture of said spatial filter for detecting remitted second wavelength radiation transmitted therethrough; and (f) interpreting a decrease in said detected remitted second wavelength radiation as an indication of the onset of coagulation of blood in the blood vessel.

16. The method of claim 15, wherein said second wavelength is about 633 nm.

17. The method of claim 15 wherein said second wavelength is about 647 nm.

18. The method of claim 15 wherein said first wavelength is between about 485 and 590 nm.

19. Apparatus for treating biological tissue by irradiation of the tissue with electromagnetic radiation having a first wavelength, the tissue to be treated including a blood vessel, the apparatus comprising:

a source of electromagnetic radiation having the first wavelength;

a first optical arrangement for directing first wavelength light from said source thereof to the biological tissue;

a source of electromagnetic radiation having a second wavelength different from the first wavelength;

a second optical arrangement for directing second wavelength light from said source thereof to the blood vessel in the biological tissue;

an optical detection arrangement for monitoring a portion of said second wavelength radiation remitted from the blood vessel; and wherein said detection arrangement is arranged to interpret one of an increase and decrease in said monitored remitted second wavelength radiation as an indication of the onset of coagulation of blood in the blood vessel.

20. The apparatus of claim 19, wherein said second wavelength is selected such that the absorptivity thereof in normal blood is greater than or equal to about two times the absorptivity thereof in methemoglobin, and wherein said detection arrangement interprets an increase in said monitored remitted second-wavelength radiation as an indication of the onset of coagulation of blood in the blood vessel.

21. The apparatus of claim 19, wherein said second wavelength is selected such that the absorptivity thereof in normal blood is less than or equal to about one-half the absorptivity thereof in methemoglobin, and wherein said detection arrangement interprets a decrease in said monitored remitted second-wavelength radiation as an indication of the onset of coagulation of blood in the blood vessel.

22. Apparatus for treating biological tissue by irradiation of the tissue with electromagnetic radiation having a first wavelength, the tissue to be treated including a blood vessel, the apparatus comprising:

a source of electromagnetic radiation having the first wavelength;

a first optical arrangement for directing first wavelength light from said source thereof to the biological tissue;

a source of electromagnetic radiation having a second wavelength between about 610 nm and 660 nm said second wavelength being different from said first wavelength;

a spatial filter having a transmitting aperture therein;

an optical system arrangement for focussing said second-wavelength radiation onto the blood vessel such that a portion of said focussed second-wavelength radiation is remitted from blood in said blood vessel, said optical system being further arranged for focussing a portion of said remitted portion of said second-wavelength into said transmitting aperture of said spatial filter;

a monitoring arrangement, said monitoring arrangement including a detector located relative to said transmitting aperture of said spatial filter for detecting remitted second-wavelength radiation transmitted therethrough; and wherein said monitoring arrangement is arranged to interpret one of an increase and decrease in said monitored remitted second wavelength radiation as an indication of the onset of coagulation of blood in the blood vessel.

23. The apparatus of claim 22, wherein said second wavelength is selected such that the absorptivity thereof in normal blood is greater than or equal to about two times the absorptivity thereof in methemoglobin, and wherein said detection arrangement interprets an increase in said monitored remitted second-wavelength radiation as an indication of the onset of coagulation of blood in the blood vessel.

24. The apparatus of claim 22 wherein said second wavelength is selected such that the absorptivity thereof in normal blood is less than or equal to about one-half the absorptivity thereof in methemoglobin, and wherein said detection arrangement interprets a decrease in said monitored remitted second-wavelength radiation as an indication of the onset of coagulation of blood in the blood vessel.

* * * * *

UNITED STATES PATENT AND TRADEMARK OFFICE
CERTIFICATE OF CORRECTION

PATENT NO. : 6,766,187 B1
DATED : July 20, 2004
INVENTOR(S) : Black, John F. et al.

It is certified that error appears in the above-identified patent and that said Letters Patent is hereby corrected as shown below:

<u>Title page,</u>
Item [54], Title, should read -- METHOD OF DETECTING COAGULATION IN LASER TREATMENT OF BLOOD VESSELS --

Signed and Sealed this

Seventh Day of September, 2004

JON W. DUDAS
*Director of the United States Patent and Trademark Office*